United States Patent
Shaban et al.

(10) Patent No.: US 12,208,153 B2
(45) Date of Patent: *Jan. 28, 2025

(54) COSMETIC COMPOSITIONS AND METHODS OF USE

(71) Applicant: Virtue Labs, LLC, Winston-Salem, NC (US)

(72) Inventors: Melisse Shaban, Winston-Salem, NC (US); William Jacobsen, Grafton, MA (US); Erin Falco, Winston-Salem, NC (US)

(73) Assignee: VIRTUE LABS, LLC, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/542,993

(22) Filed: Dec. 18, 2023

(65) Prior Publication Data

US 2024/0122836 A1    Apr. 18, 2024

Related U.S. Application Data

(60) Continuation of application No. 18/086,725, filed on Dec. 22, 2022, now Pat. No. 11,883,519, which is a division of application No. 16/018,181, filed on Jun. 26, 2018, now Pat. No. 11,534,383.

(60) Provisional application No. 62/629,341, filed on Feb. 12, 2018, provisional application No. 62/524,660, filed on Jun. 26, 2017.

(51) Int. Cl.
| | |
|---|---|
| A61K 8/65 | (2006.01) |
| A61K 8/25 | (2006.01) |
| A61K 8/27 | (2006.01) |
| A61K 8/42 | (2006.01) |
| A61K 8/64 | (2006.01) |
| A61K 8/67 | (2006.01) |
| A61K 8/73 | (2006.01) |
| A61K 8/9711 | (2017.01) |
| A61K 8/9783 | (2017.01) |
| A61Q 3/02 | (2006.01) |
| A61Q 5/00 | (2006.01) |
| A61Q 5/02 | (2006.01) |
| A61Q 5/06 | (2006.01) |
| A61Q 5/12 | (2006.01) |
| A61Q 19/08 | (2006.01) |

(52) U.S. Cl.
CPC ............... *A61K 8/65* (2013.01); *A61K 8/25* (2013.01); *A61K 8/27* (2013.01); *A61K 8/42* (2013.01); *A61K 8/645* (2013.01); *A61K 8/671* (2013.01); *A61K 8/675* (2013.01); *A61K 8/732* (2013.01); *A61K 8/9711* (2017.08); *A61K 8/9783* (2017.08); *A61Q 3/02* (2013.01); *A61Q 5/002* (2013.01); *A61Q 19/08* (2013.01); *A61Q 5/02* (2013.01); *A61Q 5/06* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 3,957,065 A * | 5/1976 | Busch | A61Q 5/04 424/70.2 |
| 4,895,722 A | 1/1990 | Abe et al. | |
| 6,270,791 B1 * | 8/2001 | Van Dyke | A61K 8/0208 424/443 |
| 2001/0006664 A1 | 7/2001 | Ensley | |
| 2001/0047082 A1 * | 11/2001 | Van Dyke | A61K 8/66 530/350 |
| 2004/0228820 A1 | 11/2004 | Elliott et al. | |
| 2005/0048015 A1 | 3/2005 | Orenga | |
| 2006/0165635 A1 | 7/2006 | Kelly et al. | |
| 2007/0074355 A1 | 4/2007 | Lee | |
| 2008/0274165 A1 * | 11/2008 | Van Dyke | A61K 38/1748 424/447 |
| 2008/0279804 A1 | 11/2008 | Parker et al. | |
| 2009/0004242 A1 * | 1/2009 | Van Dyke | A61L 31/10 424/423 |
| 2009/0211593 A1 | 8/2009 | Coppola et al. | |
| 2010/0196302 A1 | 8/2010 | Vermelho et al. | |
| 2012/0052034 A1 | 3/2012 | Azizova et al. | |
| 2014/0044664 A1 * | 2/2014 | Cardamone | A61K 8/416 132/202 |
| 2015/0011659 A1 | 1/2015 | Burnett et al. | |
| 2015/0025015 A1 | 1/2015 | Tomblyn et al. | |
| 2015/0359830 A1 | 12/2015 | Stottlemyre et al. | |
| 2016/0324750 A1 | 11/2016 | Burnett | |
| 2017/0119637 A1 | 5/2017 | Pressly | |

(Continued)

FOREIGN PATENT DOCUMENTS

| | | |
|---|---|---|
| CA | 3050635 A1 | 3/2018 |
| CN | 109846765 A | 6/2019 |
| JP | 5053543 A | 5/1975 |

(Continued)

OTHER PUBLICATIONS

Japanese Office Action for JP Application No. 2021-543991 dated Jun. 4, 2024.

(Continued)

*Primary Examiner* — Bethany P Barham
*Assistant Examiner* — Peter Anthopolos
(74) *Attorney, Agent, or Firm* — Barnes & Thornburg LLP

(57) ABSTRACT

Keratin protein cosmetic compositions are provided that include at least one keratin protein derived from human hair and a base cosmetic solution. Methods of treatment are also provided.

13 Claims, No Drawings

(56) References Cited

U.S. PATENT DOCUMENTS

| | | | |
|---|---|---|---|
| 2017/0216177 A1 | 8/2017 | Thrower | |
| 2018/0369117 A1 | 12/2018 | Shaban | |

FOREIGN PATENT DOCUMENTS

| | | | | |
|---|---|---|---|---|
| JP | 2006070019 | | 3/2016 | |
| JP | 2016160211 | A | 9/2016 | |
| JP | 2017217344 | A | 12/2017 | |
| KR | 20050084015 | A | 8/2005 | |
| KR | 20090097973 | A | 9/2009 | |
| WO | WO-2004047774 | A1 * | 6/2004 | ............... A61K 8/65 |
| WO | 2013025940 | A1 | 2/2013 | |

OTHER PUBLICATIONS

Article: "The key ingredient in this new haircare line is keratin, but where it comes from might surprise you", https://www.bustle.com/p/the-key-ingredient-in-this-new-haircare-line-is-keratin-but-where-it-comes-from-might-surpriseyou-36047, retrieved from internet on Aug. 16, 2018.

Alpha Keratin 60ku https://www.virtuelabs.com/en/alpha-keralin-60ku.html, retrieved from internet on Aug. 17, 2018.

International search report for PCT/US2018/039393, dated Sep. 11, 2018.

Hicks, T.M., et al., "Changes to Amino Acid Composition of Bloodmeal after Chemical Oxidation", RSC Adv., (2015), vol. 5, pp. 66451-66463.

Rajabinejad, H., et al., "Physicochemical Properties of Keratin Extracted from Wood by Various Methods", Textile Research Journal, (2018), vol. 88, No. 21, pp. 2415-2424.

Shavandi, A., et al., "Dissolution, Extraction and Biomedical Application of Keratin: Methods and Factors Affecting the Extraction and Physicochemical Properties of Keratin", Biomaterials Science, (May 2017), pp. 1-96.

Database GNPD [Online] Mintel; {Apr. 21, 2017), "The Perfect Ending Split End Serum" XP055773535, Database Accession No. 4697391.

European Search Report for EP Application No. 18 82 3871, dated Feb. 10, 2021.

"This New Haircare Line Uses Real Human Keratin" web page (2017). Obtained from <https://behindthechair.com/articles/ new-haircare-line-uses-real-human-keratin>.

March, B. #The Brand—Virtue Harpers Bazaar. Sep. 25, 2018: https://www.harpersbazaar.com/uk/beauty/hair/a23448978/virtue-hair-products-review/; downloaded Mar. 12, 2020.

Office action from corresponding Indian Appln. No. 2020-47003254, dated Jun. 21, 2021.

Office action from corresponding Eurasian Application No. 202090146, dated Nov. 29, 2021.

Office action from corresponding European Application No. 18823871.1, dated Jan. 21, 2022.

*Teva Pharma. USA, Inc. v. Sandoz, Inc.*, 723 F.3d 1363 (Fed. Cir. Jul. 26, 2013).

"Polymer Molecular Weight Distribution and Definitions of MW Averages", Agilent Technologies, Inc. (Apr. 30, 2015), Publication Part No. 5990-7890EN. [online] Retrieved from: https://www.agilent.com/search/?Ntt=polymer%20molecular%20weight%20distribution [retrieved on Mar. 1, 2022].

Office Action from U.S. Appl. No. 17/720,507, dated Feb. 22, 2023.

Office Action from Korean Application No. 10-2020-7002525, dated Feb. 17, 2023.

Roddick-Lanzilotta, Alisa, et al. "New keratin isolates: actives for natural hair protection." Journal of Cosmetic Science 58.4 (2007): 405-411. (Year: 2007).

Office Action for U.S. Appl. No. 17/720,507, dated Apr. 10, 2024.

Examination Report for United Arab Emirates Application No. P6000513/2021 dated Jul. 19, 2024.

\* cited by examiner

COSMETIC COMPOSITIONS AND METHODS OF USE

RELATED APPLICATIONS

This application is a continuation of U.S. application Ser. No. 18/086,725 filed Dec. 22, 2022, which is a divisional of U.S. application Ser. No. 16/018,181, now U.S. Pat. No. 11,534,383, filed Jun. 26, 2018, which claims the benefit of U.S. Provisional Patent Application Ser. No. 62/524,660 filed Jun. 26, 2017, and U.S. Provisional Patent Application Ser. No. 62/629,341 filed Feb. 12, 2018, both of which are incorporated by reference in their entirety.

BACKGROUND

Keratins are fundamental compounds of the skin, the hair, the eyelashes and the nails. These fibrous proteins contribute towards their form, elasticity and strength. Hair is a unique source of human keratins because it is one of the few human sources that are readily available and inexpensive.

Cosmetic treatments of hair substantially deteriorate and weaken the hair as well as destroy the structure of the surface of the hair. As a result, the hair dries and becomes brittle, split ends are formed or the hair may break. Hair constituent proteins may be removed by treatments with cosmetics such as shampoos, perm chemicals, or hair dyes. As a result, the likelihood of hair damage increases. Hair is unable to restore itself to its original state without assistance.

Hydrolyzed proteins may be used to condition and strengthen the hair. The actual composition, purity and molecular size of the hydrolysates is difficult to control and thus the efficacy of hydrolyzed keratin is lowered. Hydrolyzed protein may be readily washed away with water due to an extremely poor compatibility with hair.

Similar to hair, the hardness and strength of the nails, which includes fingernails and toenails, is particularly important not only for the beauty of their appearance, but for the well-being of the individual. Embrittlement of the nails is normally associated with day-to-day activities that expose the nails to a number of materials which also adversely affect the nail's physico-mechanical condition. Individuals may want to enhance and improve nails. The use of over-the-counter products can alter the nail keratin causing it to weaken, soften, split and break. Such products may also irritate the surrounding skin tissue as well as weaken and discolor the nails.

Accordingly, there remains a need for a protein product that retains structure and function and as well as methods related to the same.

SUMMARY

According to one aspect, a keratin protein cosmetic composition is provided. The keratin protein cosmetic composition includes at least one keratin protein that is derived from human hair. The keratin protein cosmetic composition also includes a cosmetic base solution. According to one embodiment, the keratin protein includes alpha-keratose, gamma-keratose, alpha-kerateine, gamma-kerateine, or a combination thereof. According to one embodiment, the keratin protein includes at least 30% alpha-keratose. According to one embodiment, the cosmetic base solution includes one or more of pink pomelo, hydrolyzed quinoa, artichoke leaf, vitamin A, vitamin C, vitamin B1, zinc, gotu kola, tapioca starch, kaolin clay, pea protein, phospholipids, brown algae, silica silylate, hydrated silica, asiaticoside/madecassoside, panthenol, cypress, baobab seed oil, or any combination thereof. According to one embodiment, the keratin protein cosmetic composition is in the form of an aqueous solution, powder, lotion, hydrogel, oil, emulsion, paste, polish or cream. According to one embodiment, the keratin protein cosmetic composition is formulated as a hair care product, body wash, shampoo, conditioner, moisturizer, deodorant, anti-aging/skin repair preparation, cleanser, toner, eye care composition, lip care composition, fingernail care composition, toenail care composition, scalp care composition, sun care composition, hand care composition, or body care composition. According to one embodiment, the keratin protein is present in an amount of about 0.01% to about 1% based on the total weight of the cosmetic composition. According to one embodiment, the keratin protein cosmetic composition includes at least 50% water based on the total weight of the cosmetic composition. According to one embodiment, the keratin protein is not denatured and maintains natural keratin protein conformation. According to one embodiment, at least about 30% of the keratin protein exhibits a molecular weight of at least about 443 KDa.

According to another aspect, a method for reducing hair breakage is provided. The method includes the steps of administering the keratin protein cosmetic composition as provided herein to a surface of the hair in need of treatment thereby increasing hair thickness and hair volume to reduce hair breakage. The hair may be styled immediately after application. The hair may also be washed between applications. According to one embodiment, the hair breakage is reduced by at least 40% after one administration.

According to another aspect, a method of reducing hair frizziness is provided. The method includes the step of administering the keratin protein cosmetic composition as provided herein to a surface of the hair in need of treatment thereby causing the hair to exhibit less frizz. The hair may be styled immediately after administration. The hair may also be washed between applications. According to one embodiment, the hair frizziness is reduced by at least 40%.

According to another aspect, a method of reducing or mending hair split ends is provided. The method includes the steps of administering the keratin protein cosmetic composition as provided herein to a surface of the hair in need of treatment. The method further includes the step of treating the hair keratin protein cosmetic composition thereby resulting in split end mending or reducing the number of split ends. According to one embodiment, at least 80% of the treated split end hair is completely mended according to the formula:

$$\% \text{ mended} = \frac{[\# \text{ of mended fibers} + \# \text{ of partially mended fibers}]}{\text{Total } \# \text{ of split end fibers taken initially.}} \times 100$$

According to another aspect, a method of hardening and strengthening the nails of a mammal is provided. The method includes the step of applying the cosmetic composition as provided herein topically to contact and coat all exposed surfaces of the nails in need of treatment to increase the hardness and strength of the nails. According to one embodiment, the method further includes the steps of maintaining the keratin protein cosmetic composition in such contact with the nail.

According to another aspect, a method of repairing or strengthening the skin of a mammal is provided. The method includes the step of applying the cosmetic composition as provided herein topically to contact and coat all exposed surfaces of the skin in need of treatment thereby repairing or strengthening the skin of the mammal. According to one embodiment, the method further includes the steps of maintaining the keratin protein cosmetic composition in such contact with the skin.

DETAILED DESCRIPTION

One or more aspects and embodiments may be incorporated in a different embodiment although not specifically described. That is, all aspects and embodiments can be combined in any way or combination. When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, the term "keratin protein source" includes proteinaceous sources of keratin proteins from human hair. The human hair can be end-cut, as one would typically find in a barber shop or salon.

As used herein, the term "keratin protein(s)" as used herein collectively refers to hair protein sources, including but not limited to naturally occurring keratin, reduced keratin, oxidized keratin, S-sulfonated keratin, or a combination thereof. This term also refers to the extracted keratin derivatives that are produced by oxidative and/or reductive treatment of keratin, including but not limited to keratose, alpha-keratose, gamma-keratose, kerateines, alpha-kerateine, or gamma-kerateine. Soluble keratins can be extracted from human hair fibers by oxidation or reduction using methods known in the art. If one employs an oxidative treatment, the resulting keratins are referred to as "keratoses." If a reductive treatment is used, the resulting keratins are referred to as "kerateines."

The terms "alpha keratin" and "alpha keratose" may be used interchangeably. The alpha keratin typically has a molecular weight range from about 500 Da to about 6.2 MDa.

According to one embodiment, a method for the production of a keratin protein composition is provided. The method includes the step obtaining or providing a keratin protein source. The keratin protein source is human hair. According to one embodiment, the human hair is of Asian origin. The keratin protein source is not derived from other sources such as, for example, wool, fur, horns, hooves, beaks, feathers, scales.

According to one embodiment, the method further includes the step of bleaching human hair to remove color. According to one embodiment, an oxidant is added to the bleached hair and mixed. The oxidized hair is then rinsed to remove residual oxidant. According to one embodiment, the rinsed hair is then washed in an aqueous solution to release the water soluble proteins from the hair into a liquid extract.

According to one embodiment, the method further includes the step of separating and dialyzing the liquid extract resulting in a soluble keratin protein solution. According to one embodiment, the keratin protein is alpha-keratose, gamma-keratose, kerateines, alpha-kerateine, gamma-kerateine, or a combination thereof. According to one embodiment, the method further includes the step of adding at least one preservative.

According to a particular embodiment, the keratin protein derived according to the methods herein is predominantly alpha keratose. According to a particular embodiment, the keratin protein content is at least about 30% alpha keratose. According to a particular embodiment, the keratin protein content is at least about 40% alpha keratose. According to a particular embodiment, the keratin protein content is at least about 50% alpha keratose. According to a particular embodiment, the keratin protein content is at least about 60% alpha keratose. According to a particular embodiment, the keratin protein content is at least about 70% alpha keratose. According to a particular embodiment, the keratin protein content is at least about 80% alpha keratose. According to a particular embodiment, the keratin protein content is at least about 90% alpha keratose. According to a particular embodiment, the keratin protein content is at least about 99% alpha keratose. According to a particular embodiment, the keratin protein content is at least about 100% alpha keratose. According to one embodiment, the cosmetic composition is substantially free of gamma-keratose.

According to a particular embodiment, the keratin protein is predominantly alpha kerateine. According to a particular embodiment, the keratin protein content is at least about 30% alpha kerateine. According to a particular embodiment, the keratin protein content is at least about 40% alpha kerateine. According to a particular embodiment, the keratin protein content is at least about 50% alpha kerateine. According to a particular embodiment, the keratin protein content is at least about 60% alpha kerateine. According to a particular embodiment, the keratin protein content is at least about 70% alpha kerateine. According to a particular embodiment, the keratin protein content is at least about 80% alpha kerateine. According to a particular embodiment, the keratin protein content is at least about 90% alpha kerateine. According to a particular embodiment, the keratin protein content is at least about 99% alpha kerateine. According to a particular embodiment, the keratin protein content is at least about 100% alpha kerateine. According to one embodiment, the cosmetic composition is substantially free of gamma-kerateine.

According to one embodiment, the keratin protein as provided herein is not precipitated during production of the keratin protein composition. According to one embodiment, the keratin protein maintains a naturally occurring shape or configuration (i.e., does not undergo any transformation or denaturing) during extraction from human hair and subsequent processing. According to one embodiment, the keratin protein does not undergo any transformation or denaturing during extraction from human hair and subsequent processing. The extraction process ensure the harvested proteins are of correct conformation structure. According to one embodiment, the keratin proteins as provided herein are substantially or completely soluble in water. Still further, the keratin proteins provided herein exhibit improved performance for the treatment and repair of hair, skin and nails compared to compositions that include denatured keratin proteins. According to one embodiment, the keratin proteins can be freeze-dried or lyophilized to form a powder formulation or added to a base solution or carrier as provided herein to form an appropriate keratin protein cosmetic composition for application to hair, skin or nails.

According to one embodiment, the keratin protein as provided herein exhibits a molecular weight of from typically about 500 Da to about 6.2 MDa. According to a particular embodiment, at least about 30% of the keratin protein exhibits a molecular weight of at least about 443 KDa. According to a particular embodiment, at least about 40% of the keratin protein exhibits a molecular weight of at least about 443 KDa. According to a particular embodiment, at least about 50% of the keratin protein exhibits a molecular weight of at least about 443 KDa. According to a particular embodiment, at least about 60% of the keratin protein exhibits a molecular weight of at least about 443 KDa. According to a particular embodiment, at least about 70% of the keratin protein exhibits a molecular weight of at least about 443 KDa. According to a particular embodiment, at least about 80% of the keratin protein exhibits a molecular weight of at least about 443 KDa. According to a particular embodiment, at least about 90% of the keratin protein exhibits a molecular weight of at least about 443 KDa.

According to one embodiment, a cosmetic composition is provided. According to one embodiment, the cosmetic composition includes a keratin protein composition as provided herein. According to one embodiment, the cosmetic composition further includes a base solution. The base solution may include one more ingredients that do not impact or change the shape of conformation of the keratin protein. Such ingredients may include one or more naturally occurring components. The base solution may include one or more of pink pomelo, hydrolyzed quinoa, artichoke leaf, vitamin A, vitamin C, vitamin B1, zinc, gotu kola, tapioca starch, kaolin clay, pea protein, phospholipids, brown algae, silica silylate, hydrated silica, asiaticoside/madecassoside, panthenol, cypress, baobab seed oil, or any combination thereof. The base solution may also include one or more of tocopherol, dimethicone, parabens, titanium dioxide, sodium lauryl sulphate, sodium laureth sulphate, retinol, collagen, ambergris, squalene, cochineal dye, guanine, tallow, gelatin, lanolin, citric acid, sodium citrate, cocamide, guar gum, xanthum gum, glycol distearate, polyglycol esters, sodium chloride, glycerin, cetyl alcohol, stearyl alcohol, panthenol, silicones, or any combination thereof. The base solution may also include one or more of D-panthenol, polysorbate 20, cetyl alcohol, Crambe abyssinica seed oil, hydroxyethyl acrylate/sodium acryloyldimethyl tau rate copolymer, isohexadecane, polysorbate 60, cyclopentasiloxane, cyclohexasiloxane, C11-13 isoparaffin, dimethiconol, isohexadecane, dimethicone, caprylyl glycol, phenoxyethanol, hexylene glycol, or any combination thereof. The base solution may include one or more of the cosmetic additives, polymers, solvents, or film forming agents as described herein.

According to one embodiment, the keratin protein cosmetic composition includes at least one preservative. Suitable preservatives include, but are not limited to, any preservative that is acceptable for cosmetic purposes. The at least one preservative may be present in an amount of from about 0.1% to about 99% based on the total weight of the keratin protein cosmetic composition.

According to one embodiment, the keratin protein cosmetic composition includes water. According to a particular embodiment, the water is sterile. The water is present in an amount from 0.1% to about 99.9% based on the total weight of the keratin protein cosmetic composition. According to one embodiment, the keratin protein cosmetic composition includes at least 50% water based on the total weight of the keratin protein cosmetic composition. According to one embodiment, the keratin protein cosmetic composition includes at least 60% water based on the total weight of the keratin protein cosmetic composition. According to one embodiment, the keratin protein cosmetic composition includes at least 70% water based on the total weight of the keratin protein cosmetic composition. According to one embodiment, the keratin protein cosmetic composition includes at least 80% water based on the total weight of the keratin protein cosmetic composition. According to one embodiment, the keratin protein cosmetic composition includes at least 90% water based on the total weight of the keratin protein cosmetic composition.

According to one embodiment, the keratin protein cosmetic composition as provided herein may include at least about 0.01% to about 100% keratin protein based on the total weight of the keratin protein cosmetic composition. According to one embodiment, the keratin protein composition as provided herein may include from about 0.01% to about 10% keratin protein based on the total weight of the keratin protein cosmetic composition. According to one embodiment, the keratin protein composition as provided herein may include from about 0.01% to about 1.00% keratin protein based on the total weight of the keratin protein cosmetic composition. According to one embodiment, the keratin protein is alpha-keratose, gamma-keratose, kerateins, alpha-kerateine, gamma-kerateine, or any combination thereof. According to one embodiment, the keratin protein composition is substantially viscous at both ambient temperature and at about 3° C.

According to one embodiment, the cosmetic composition further includes one or more cosmetic additives. The cosmetic additives do not themselves change the functional properties of any keratin protein present in the cosmetic composition. Suitable cosmetic additives include, but are not limited to, non-ionic, anionic or cationic polymers, preservatives, oils, pH regulators, waxes, fragrances, antifatting agents, sequestrating agents, perfumes, dyes, cationic surfactants, proteins, silicones, surfactants, organic solvents and any other additive conventionally used in the cosmetics field. According to one embodiment, the at least cosmetic additive is present in an amount of between 0.01 and 50% based on the total weight of the keratin protein cosmetic composition.

According to one embodiment, the cosmetic composition includes one or more polymers to provide hold to the hair. Suitable polymers include, but are not limited to, nonionic polymers such as polyvinylpyrrolidones, copolymers of polyvinylpyrrolidone and vinyl acetate, and anionic polymers such as copolymers of vinyl acetate and an unsaturated carboxylic acid such as crotonic acid, copolymers resulting from copolymerisation of vinyl acetate, crotonic acid and an acrylic or methacrylic ester, copolymers resulting from copolymerisation of vinyl acetate, an alkoylvinyl ether and an unsaturated carboxylic acid and copolymers resulting from copolymerisation of vinyl acetate, crotonic acid and a vinyl ester of a long carbon chain acid or an allyl or methallyl ester of a long carbon chain acid. According to one embodiment, the at least one polymer is present in an amount of between 0.01 and 50% based on the total weight of the keratin protein cosmetic composition.

According to one embodiment, the cosmetic composition includes one or more cosmetically acceptable solvents. Suitable cosmetically acceptable solvents include low alcohols, for example ethanol or isopropanol, glycerol, glycols or glycol ethers such as the monobutyl ether of ethyleneglycol, propyleneglycol, or the monoethylether or the monomethylether of diethyleneglycol, in proportions which do not affect gel formation According to one embodiment, the at least one cosmetically acceptable solvent is present in an amount of between about 0.01% and about 99.9% based on the total weight of the keratin protein cosmetic composition.

According to one embodiment, the cosmetic composition may further include at least one additional additives. Suitable additional additives include, but are not limited to, solid emollients, emulsifiers, surface active agent, gum, humectant, thickener, powder diluent, dispersant, or carrier so as to facilitate the distribution of the composition when applied.

According to one embodiment, the at least one additional additive is present in an amount of between about 0.1% and about 99.9% based on the total weight of the keratin protein cosmetic composition.

According to one embodiment, the cosmetic composition may further include a film forming agent. Suitable film forming agents include, but are not limited to, liquid or solid emollient, emulsifiers, surface active agents, gums, humectants, thickeners, powders and protein solutions. Suitable emollients include mineral oil, fatty alcohols, alkyl esters, silicones and silicone derivatives. According to one embodiment, the at least one film forming agent is present in an amount of between about 0.01% and about 99.9% based on the total weight of the keratin protein cosmetic composition.

According to one embodiment, the cosmetic composition may be formulated to be applied to any part of the body where a cosmetic application is acceptable. According to one embodiment, the cosmetic composition may be formulated as an aqueous solution, powder, lotion, hydrogel, oil, emulsion, paste, polish or cream. According to one embodiment, the cosmetic compositions as provided herein may be formulated as hair care products such as shampoo and conditioner, moisturizer, a deodorant, an anti-aging/skin repair preparation, a cleanser, a toner, an eye care composition, a lip care composition, a fingernail care composition, a toenail care composition, a scalp care composition, a sun care composition (e.g., sunscreen), a hand care composition, or a body care composition.

The compositions according to present invention are suitable for various cosmetic purposes on the exterior of a mammalian body. According to one embodiment, the cosmetic compositions provided herein may be utilized for the treatment of keratin-comprising structures and tissues. According to a preferred embodiment, the cosmetic compositions provided herein may be utilized for the treatment of hair, nails, skin or any combination thereof. According to one embodiment, the cosmetic compositions as provided herein may be utilized to strengthen or improve the overall appearance and health of a mammal's hair, nails, skin. According to one embodiment, the cosmetic compositions as provided herein may be utilized to prevent breakage of a mammal's hair, nails, skin. According to one embodiment, the cosmetic compositions as provided herein may be utilized to reduce or prevent split or frayed ends of a mammal's hair. According to one embodiment, the cosmetic compositions as provided herein may be utilized to enhance the color or color vibrancy of hair.

Various methods of treatment of a mammal's hair, nails, skin are also provided. According to one embodiment, a method of improving the strength of a mammal's hair, nails, skin is provided. The method includes the step of administering, applying or otherwise introducing the cosmetic composition to the surface of a mammal's hair, nails, skin or any combination thereof in need of treatment.

According to another aspect, a method for reducing hair breakage is provided. The method includes the steps of administering the keratin protein cosmetic composition as provided herein to a surface of the hair in need of treatment thereby increasing hair thickness and hair volume to reduce hair breakage. The hair may be styled immediately after application. The hair may also be washed between applications. According to one embodiment, the hair breakage is reduced by at least 40% after one administration.

According to another aspect, a method of reducing hair frizziness is provided. The method includes the step of administering the keratin protein cosmetic composition as provided herein to a surface of the hair in need of treatment thereby causing the hair to exhibit less frizz. The hair may be styled immediately after application. The hair may also be washed between applications. According to one embodiment, the hair frizziness is reduced by at least 40%.

According to another aspect, a method of reducing or mending hair split ends is provided. The method includes the steps of administering the keratin protein cosmetic composition as provided herein to a surface of the hair in need of treatment thereby resulting in split end mending or reducing the number of split ends. The hair may be styled immediately after application. The hair may also be washed between applications. According to one embodiment, at least 80% of the treated split end hair is completely mended according to the formula:

$$\% \text{ mended} = \frac{[\# \text{ of mended fibers} + \# \text{ of partially mended fibers}]}{\text{Total \# of split end fibers taken initially.}} \times 100$$

According to another aspect, a method of hardening and strengthening the nails of a mammal is provided. The method includes the step of applying the cosmetic composition as provided herein topically to contact and coat all exposed surfaces of the nails in need of treatment to increase the hardness and strength of the nails. According to one embodiment, the method further includes the steps of maintaining the keratin protein cosmetic composition in such contact with the nail. According to one embodiment, the keratin protein cosmetic composition is allowed to remain in contact with the nail without taking any steps to remove any excess composition.

According to another aspect, a method of repairing or strengthening the skin of a mammal is provided. The method includes the step of applying the cosmetic composition as provided herein topically to contact and coat all exposed surfaces of the skin in need of treatment thereby repairing or strengthening the skin of the mammal. According to one embodiment, the method further includes the steps of maintaining the keratin protein cosmetic composition in such contact with the skin. According to one embodiment, the keratin protein cosmetic composition is allowed to remain in contact with the skin without taking any steps to remove any excess composition.

According to another aspect, a method of increasing hair strand thickness is provided. The method includes the step of administering, applying or otherwise introducing the cosmetic composition to the surface of a mammal's hair in need of treatment.

According to another aspect, a method of increasing hair strand volume is provided. The method includes the step of administering, applying or otherwise introducing the cosmetic composition to the surface of a mammal's hair in need of treatment.

According to another aspect, a method of retaining hair gloss is provided. The method includes the step of administering, applying or otherwise introducing the cosmetic composition to the surface of a mammal's hair in need of treatment.

According to another aspect, a method of improving hair color concentration is provided. The method includes the step of administering, applying or otherwise introducing the cosmetic composition to the surface of a mammal's hair in need of treatment.

According to one embodiment, a method of reducing skin irritation, skin inflammation or skin pain is provided. The method includes the step of administering, applying or otherwise introducing the cosmetic composition to the surface of a mammal's skin that is in need of treatment. The skin irritation may be caused by a scratch, injury, surgical site or sunburn.

According to one embodiment, a method of reducing the appearance of skin scarring is provided. The method includes the step of administering, applying or otherwise introducing the cosmetic composition to the surface of a mammal's skin that is in need of treatment.

According to one embodiment, a method of increasing nail growth rate in provided. The method includes the step of administering, applying or otherwise introducing the cosmetic composition to the surface of a mammal's nail that is in need of treatment.

All publications, patents and patent applications cited in this specification are incorporated herein by reference for the teaching to which such citation is used.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Example 1

Testing was conducted to evaluate the breakage of hair based on repeated grooming. The number of broken fibers was recorded as a function of repeated combing/brushing strokes. Any treatment that reduces snags, entanglements and abrasion aids in substantially lowering the number of broken fibers. A custom-built automated grooming device was utilized that included a hollow rotating drum-like assembly where four outer crossbars contained holders for mounting combs or brushes. These outer arms were detachable to allow for different holders to be mounted and experiments to be performed using a variety of combs or brushes. Four combs or brushes were mounted at 90 degree angles—allowing one complete drum revolution to comb (or brush) a tress four times. This entire set-up was duplicated three times in the horizontal direction allowing four tresses to be combed simultaneously. Collection plates were located under each tress to save broken fiber fragments, while spacer plates on the rotating drum prevented cross contamination. All experiments were again performed after overnight equilibration of the hair at 60% relative humidity. Tresses were repeatedly brushed 2,000 times with broken fibers being evaluated every 200 strokes. Ten replicate hair tresses were used for each sample to ensure statistical relevance. This methodology had also been documented in the scientific literature (Evans & Park, *A Statistical Analysis of Hair Breakage. II. Repeated Grooming Experiments, J. Cosmet. Sci.,* 61, 439-455, 2010).

All testing was performed on hair procured from International Hair Importers & Products (Glendale, NY). Prior to testing, the tresses were bleached with 9% Hydrogen peroxide at a pH of 10.2. The tresses were left in contact with the hydrogen peroxide solution for 20 minutes at 40° C. The tresses were then rinsed at 40° C. with a controlled rate of 1.0 GPM. The bleaching procedure was then repeated twice more.

Mulatto hair tresses subject to testing were 3 g in weight and 8" in length. Fine hair tresses subject to testing were 3 g in weight and 8" in length. Tresses were standardized with 0.3 m/tress of SLES with a 30 second massage and 30 second rinse prior to treatment.

A cosmetic base solution (control) was applied to the Mulatto hair and compared to a keratin protein composition (0.5% keratin protein) that was applied to Mulatto hair. The cosmetic base solution included water, D-panthenol, polysorbate 20, cetyl alcohol, *Crambe abyssinica* seed oil, hydroxyethyl acrylate/sodium acryloyldimethyl tau rate copolymer, isohexadecane, polysorbate 60, cyclopentasiloxane, cyclohexasiloxane, C11-13 isoparaffin, dimethiconol, isohexadecane, dimethicone, caprylyl glycol, phenoxyethanol, and hexylene glycol.

The keratin protein composition was prepared as provided herein with the same cosmetic base solution (control). A box and whisker plot was generated using Statistica™, while JMP™ analytical software was used to calculate the statistics (student's t-test at 95% confidence level). The percent reduction in breakage may be calculated as follows:

$$\% \text{ reduction in brokerage} = 1 - \frac{\text{mean \# broken fibers of treatment}}{\text{mean \# broken fibers of control}} \times 100$$

The results below (Table 1) showed Mulatto hair treated with a 0.5% keratin protein composition provided a statistically significantly lower breakage compared to the control cosmetic base solution (42.6% reduction in breakage according to the formula above). Thus, the keratin protein composition provides as a statistically significant reduction in the breakage of hair (compared to base cosmetic compositions) from repeated grooming thereby showing that application results in less broken or damaged hair with more hair being left on the head of a user.

TABLE 1

| Treatment | Number of treatments | Mean number of Broken Fibers | Standard Deviation |
|---|---|---|---|
| Control base solution | 10 | 54.00 | 3.87 |
| Base solution + 0.5% Keratin protein composition | 10 | 31.30 | 1.74 |

A cosmetic base solution (control) was applied to fine hair and compared to a keratin protein composition (0.5% keratin protein) that was applied to fine hair. The cosmetic base solution included water, D-panthenol, polysorbate 20, cetyl alcohol, *Crambe abyssinica* seed oil, hydroxyethyl acrylate/sodium acryloyldimethyl tau rate copolymer, isohexadecane, polysorbate 60, cyclopentasiloxane, cyclohexasiloxane, C11-13 isoparaffin, dimethiconol, isohexadecane, dimethicone, caprylyl glycol, phenoxyethanol, and hexylene glycol.

The keratin protein cosmetic composition was prepared as provided herein with the same cosmetic base solution (control). A box and whisker plot was generated using Statistica™, while JMP™ analytical software was used to calculate the statistics (student's t-test at 95% confidence level). The percent reduction in breakage was calculated as noted above.

The results below (Table 2) showed fine treated with a 0.5% keratin protein cosmetic composition provided a statistically significantly lower breakage compared to the control cosmetic base solution (41.6% reduction in breakage according to the formula above). Thus, the keratin protein composition provided as a statistically significant reduction in the breakage of hair (compared to base cosmetic compositions) from repeated grooming thereby showing that application resulted in less broken or damaged hair with more hair being left on the head of a user.

TABLE 2

| Treatment | Number of treatments | Mean number of Broken Fibers | Standard Deviation |
|---|---|---|---|
| Control base solution | 10 | 35.80 | 6.2 |
| Base solution + 0.5% Keratin protein composition | 10 | 20.90 | 4.18 |

Example 2

Testing was conducted to evaluate and compare the split end mending of hair. The hair utilized was 5 grams of 10" double bleached Caucasian hair. Each test sample was treated with the 1.0 mL of the respective hair and left to dry overnight at 21° C. and 60% controlled relative humidity. Fifty (50) fibers with split ends were randomly selected with each one individually labeled for tracking purposes. Each of the split ends fibers were then imaged. The tresses were then treated with a 0.5% and 1.0% keratin protein cosmetic composition as provided herein. Images were taken both before and after treatment. Particularly, the split end of each fiber was imaged using a 25× stereo microscope. The tresses were graded and judged according to a visual evaluation scale to help describe the state of the fibers as set forth in Table 3.

TABLE 3

| Rate | Repair |
|---|---|
| 1 | No Repair |
| 2 | Minimal partial repair = less than 30% angle repair |

TABLE 3-continued

| Rate | Repair |
|---|---|
| 3 | Moderate degree of partial repair = between 30% and 70% angle repair |
| 4 | Reasonable degree of partial repair = more than 70% angle repair |
| 5 | Complete Repair |

A percentage of mending was then be calculated using the formula as follows:

$$\% \text{ mended} = \frac{[\# \text{ of mended fibers} + \# \text{ of partially mended fibers}]}{\text{Total \# of split end fibers taken initially}} \times 100$$

The values obtained for the control, 0.5% keratin protein composition and 1.0% protein composition are provided in Table 4.

TABLE 4

| Treatment | Total No. of Fibers | No. of Fibers partially amended (i.e., >30% angle reduction (3, 4)) | No. of Fibers Completely Mended (5) | Total % of split ends (i.e., >30% angle reduction (3, 4)) | % of split ends completely mended (5) |
|---|---|---|---|---|---|
| 0.5% Keratin protein composition | 49 | 3 | 42 | 92 | 86 |
| 1.0% Keratin protein composition | 50 | 10 | 39 | 98 | 78 |

The data obtained demonstrates that split ends treated with a 0.5% keratin protein composition exhibit a total of 92% of split end mending (>30% reduction in angle) and 86% showed a complete repair of the split end. Split ends treated with a 1.0% keratin protein composition shows a total of 98% of split end mending (>30% reduction in angle) and 78% show a complete repair of the split end. The data illustrates that the keratin protein cosmetic compositions are effective at mending and repairing split ends.

Example 3

Testing was conducted to evaluate the efficacy and improvement of the overall condition and appearance of hair. Each stage in the progression of treatment was photographically documented then analyzed using High Resolution Scientifically Matched Photography and PhotoGrammetrix™ Image Analysis. In addition, the effectiveness of the treatment was evaluated via visual expert grading and subjectively using panelist self-assessment questionnaire responses. The Expert Grading Scale allowed the evaluator to grade the subjects' hair for a number of visual and tactile parameters including: hair body, damage/split end repair, hair volume, hair frizz, hair softness, hair thickness appearance, hair thickness feel, hair shine, and hair hold using the same 11-point intensity grading scale used at baseline where 0=Worst Condition Imaginable and 10=Best Condition Imaginable.

The groups of individuals with following hair type participated in the study:
Group I: fine hair
Group 2: damaged hair
Group 3: curly/frizzy hair Fifteen healthy female subjects between the ages of 25 and 57 were inducted into this study. The study was conducted according to a randomized block, single-blind design, where the participants were not aware of which side of the head received the control base cosmetic composition and which was treated with a 0.5% keratin protein cosmetic composition. About one fourth to about one half ounce of control or 0.5% keratin protein cosmetic composition was applied to the respective side of each test subjects head of hair. The hair was freshly shampooed and towel dried before treatment. The control and 0.5% keratin protein cosmetic composition were combed through and distributed from roots to ends and blown dry. The aforementioned treatments were continued for four consecutive days post initial application. Prior to the initial treatment and after each application, each subject was given a subjective questionnaire, subjected to expert grading and photography.

For the Group 1 subjects, data obtained from PhotoGrammetrix™ Image Analysis demonstrated that the 0.5% keratin protein cosmetic composition was effective in increasing hair strand volume on the treated sites. Particularly, test subjects reporting an average of 10% increase in hair strand thickness. The Group 1 subjects also reported an average of 6% increase in hair strand volume. Finally, the Group 1 subjects reported a retained hair gloss of 93%.

For the Group 2 subjects, data obtained from PhotoGrammetrix™ Image Analysis demonstrated that the 0.5% keratin protein cosmetic composition was effective in split end repair on the treated sites (99.8%). Data obtained from PhotoGrammetrix™ Image Analysis also demonstrated that the 0.5% keratin protein cosmetic composition was effective in improving color concentration on the treated sites (18%). Color would be expected to fade over the four days of the study.

For Group 3, data obtained from PhotoGrammetrix™ Image Analysis demonstrated that the 0.5% keratin protein cosmetic composition was effective in reducing hair frizziness on the treated sites. Data obtained from PhotoGrammetrix™ Image Analysis demonstrated that the 0.5% keratin protein cosmetic composition was effective in improving hair manageability. Particularly, subjects experienced a 41% reduction in frizz over the course of the study. Data obtained from PhotoGrammetrix™ Image Analysis demonstrated that the 0.5% keratin protein cosmetic composition was effective in improving color concentration on the treated sites. Particularly, color concentration was improved by an average of 36% over the course of the study. The subjective questionnaire responses corroborate the aforementioned conclusions with the majority of responses consistent with the Expert Grading and PhotoGrammetrix™ results.

Example 4

A keratin protein cosmetic composition was prepared as provided herein. The cosmetic composition was applied to a human subject's skin that was burned from exposure (sunburn). The subject observed reduced redness, a shortened period of skin irritation, and a reduction in pain.

Example 5

A keratin protein cosmetic composition was prepared as provided herein. The cosmetic composition was applied to a human subject's skin that was scarred. The subject observed a reduction in observability of the scar.

Example 6

A keratin protein cosmetic composition was prepared as provided herein. The cosmetic composition was applied to a human subject's skin that was inflamed. The subject observed reduced inflammation.

Example 7

A keratin protein cosmetic composition was prepared as provided herein. The cosmetic composition was applied to a human subject's nails. The subject observed an increased speed of nail growth and an improvement in nail appearance and quality.

Example 8

Keratin protein extracted according to the methods provided herein were extensively characterized. Three-dimensional conformational testing was conducted using circular dichroism. The keratin protein conformational structure was found to be consistent with a protein in an alpha helical form. Thus, the results were conclusive in supporting the conformational structure of the alpha keratin protein.

What is claimed is:

1. A method of retaining hair gloss comprising the steps of:
    administering a keratin protein cosmetic composition to a surface of the hair in need of treatment; and
    rinsing the hair to remove any excess keratin protein cosmetic composition thereby retaining hair gloss,
    wherein the keratin protein cosmetic composition comprises:
        at least one keratin protein derived from human hair; and
        a cosmetic base solution,
    wherein the keratin protein is not denatured and maintains natural keratin protein conformation, and
    wherein at least about 30% of the keratin protein exhibits a molecular weight of at least about 443 KDa.

2. The method of claim 1, wherein at least 30% of the keratin protein exhibits a molecular weight within the range of from about 443 KDa to about 6.2 MDa.

3. The method of claim 1, wherein the keratin protein comprises alpha-keratose, gamma-keratose, alpha-kerateine, gamma-kerateine, or a combination thereof.

4. The method of claim 1, wherein the keratin protein cosmetic composition is formulated as an aqueous solution, powder, lotion, hydrogel, oil, emulsion, paste, polish or cream.

5. A method of improving hair color concentration comprising the steps of:
    administering a keratin protein cosmetic composition to a surface of the hair in need of treatment; and
    rinsing the hair to remove any excess keratin protein cosmetic composition thereby concentrating hair color,
    wherein the keratin protein cosmetic composition comprises:
        at least one keratin protein derived from human hair; and
        a cosmetic base solution,
    wherein the keratin protein is not denatured and maintains natural keratin protein conformation, and
    wherein at least about 30% of the keratin protein exhibits a molecular weight of at least about 443 KDa.

6. The method of claim 5, wherein at least 30% of the keratin protein exhibits a molecular weight within the range of from about 443 KDa to about 6.2 MDa.

7. The method of claim 5, wherein the keratin protein comprises alpha-keratose, gamma-keratose, alpha-kerateine, gamma-kerateine, or a combination thereof.

8. The method of claim 5, wherein the keratin protein cosmetic composition is formulated as an aqueous solution, powder, lotion, hydrogel, oil, emulsion, paste, polish or cream.

9. A method of reducing skin irritation, skin inflammation or skin pain comprising the steps of:
- administering a keratin protein cosmetic composition to a surface of the skin in need of treatment; and
- rinsing the skin to remove any excess keratin protein cosmetic composition thereby resulting in split end mending or reducing the number of split ends
- wherein the keratin protein cosmetic composition comprises:
  - at least one keratin protein derived from human hair; and
  - a cosmetic base solution,
- wherein the keratin protein is not denatured and maintains natural keratin protein conformation, and
- wherein at least about 30% of the keratin protein exhibits a molecular weight of at least about 443 KDa.

10. The method of claim 9, wherein at least 30% of the keratin protein exhibits a molecular weight within the range of from about 443 KDa to about 6.2 MDa.

11. The method of claim 9, wherein the keratin protein comprises alpha-keratose, gamma-keratose, alpha-kerateine, gamma-kerateine, or a combination thereof.

12. The method of claim 9, wherein the keratin protein cosmetic composition is formulated as an aqueous solution, powder, lotion, hydrogel, oil, emulsion, paste, polish or cream.

13. The method of claim 9, wherein the skin irritation is caused by a scratch, injury, surgical site or sunburn.

* * * * *

UNITED STATES PATENT AND TRADEMARK OFFICE
CERTIFICATE OF CORRECTION

PATENT NO. : 12,208,153 B2
APPLICATION NO. : 18/542993
DATED : January 28, 2025
INVENTOR(S) : Shaban et al.

Page 1 of 1

It is certified that error appears in the above-identified patent and that said Letters Patent is hereby corrected as shown below:

In the Claims

Column 15, Claim 9, Line 10, please delete "split end mending or reducing the number of split ends" and insert --reduced skin irritation, skin inflammation or skin pain--.

Signed and Sealed this
Twenty-fifth Day of February, 2025

Coke Morgan Stewart
*Acting Director of the United States Patent and Trademark Office*